United States Patent
Yoo et al.

(10) Patent No.: US 12,319,937 B2
(45) Date of Patent: Jun. 3, 2025

(54) COMPOSITION AND METHOD FOR CULTURING ORGANOIDS

(71) Applicant: ORGANOIDSCIENCES, LTD., Gyeonggi-do (KR)

(72) Inventors: Jong-Man Yoo, Seongnam-si (KR); Soo-Jung Han, Seongnam-si (KR); Myoung-Ok Nam, Daegu (KR)

(73) Assignee: ORGANOIDSCIENCES, LTD., Gyeonggi-do (KR)

( * ) Notice: Subject to any disclaimer, the term of this patent is extended or adjusted under 35 U.S.C. 154(b) by 536 days.

(21) Appl. No.: 16/618,268

(22) PCT Filed: May 29, 2018

(86) PCT No.: PCT/KR2018/006057
§ 371 (c)(1),
(2) Date: Apr. 6, 2020

(87) PCT Pub. No.: WO2018/221918
PCT Pub. Date: Dec. 6, 2018

(65) Prior Publication Data
US 2020/0385683 A1    Dec. 10, 2020

(30) Foreign Application Priority Data

May 29, 2017   (KR) ........................ 10-2017-0065782

(51) Int. Cl.
*C12N 5/071* (2010.01)
*C07D 473/10* (2006.01)

(52) U.S. Cl.
CPC ......... *C12N 5/0679* (2013.01); *C07D 473/10* (2013.01); *C12N 2501/999* (2013.01); *C12N 2513/00* (2013.01)

(58) Field of Classification Search
CPC ............ C12N 5/0679; C12N 2501/999; C07D 473/10
See application file for complete search history.

(56) References Cited

FOREIGN PATENT DOCUMENTS

| KR | 10-2014-0138221 A | 12/2014 |
| KR | 10-2016-0006167 A | 1/2016 |
| WO | 2015/157376 A1 | 10/2015 |

OTHER PUBLICATIONS

PubChem, 3,7-Dimethyl-8-quinolin-2-ylsulfanylpurine-2,6-dione (RS-246204) compound summary. Accessed from internet, Apr. 1, 2022. (Year: 2006).*
Clevers, Modeling development and disease with organoids, Cell, 165: 1586-1597. (Year: 2016).*
Yin et al., Engineering stem cell organoids, Cell Stem Cell, 7: 18: 25-38. (Year: 2016).*
Lesavage et al., Next-generation cancer organoids, Nature Materials, 21: 143-159. (Year: 2022).*
Lancaster et al., Organogenesis in a dish: modeling development and disease using organoid technologies, Science, 345 (6194): 1247125-1-1247125-9. (Year: 2014).*
Rezakhani et al., Extracellular matrix requirements for gastrointestinal organoid cultures, Biomaterials, 276: p. 1-13. (Year: 2021).*
Pastula et al., Three-Dimensional Gastrointestinal Organoid Culture in Combination with Nerves or Fibroblasts: A Method to Characterize the Gastrointestinal Stem Cell Niche, Stem Cells International, vol. 2016, p. 1-16 (Year: 2016).*
Mahe et al., Establishment of gastrointestinal epithelial organoids, Curr Protoc Mouse Biol, 3: 217-240. (Year: 2014).*
Chemical Abstract compounds, STN express RN 878451-87-7 (Entered Date: Mar. 29, 2006) RN 852536-84-6 (Entered Date: Jun. 20, 2005).
Myeong-Ok Nam et al., "Effects of a small molecule R-spondin-1 substitute RS-246204 on a mouse intestinal organoid culture", Oncotarget, 2018, pp. 6356-6368, vol. 9, No. 5.
Notification of Reason for Refusal of Korean Application No. 10-2017-0065782 dated Sep. 21, 2018.
International Search Report of PCT/KR2018/006057 dated Aug. 29, 2018 [PCT/ISA/210].

* cited by examiner

*Primary Examiner* — Arthur S Leonard
*Assistant Examiner* — Joseph Paul Miano
(74) *Attorney, Agent, or Firm* — Sughrue Mion, PLLC

(57) ABSTRACT

The present invention relates to a composition for culturing organoids and a method for culturing organoids by using the same. Since the present invention includes a compound, which can replace an essential protein component in a conventional medium, consistent stability during organoid culturing can be maintained and culturing can be performed at low cost.

5 Claims, 6 Drawing Sheets
(1 of 6 Drawing Sheet(s) Filed in Color)

COMPOSITION AND METHOD FOR CULTURING ORGANOIDS

CROSS REFERENCE TO RELATED APPLICATIONS

This application is a National Stage of International Application No. PCT/KR2018/006057, filed May 29, 2018, claiming priority to Korean Patent Application No. 10-2017-0065782, filed May 29, 2017, the disclosure of which is incorporated herein by reference in its entirety.

TECHNICAL FIELD

The present disclosure provides a composition for culturing organoids and a method for culturing organoids by using the same.

BACKGROUND ART

Stem cells are of great interest since they can be used in various fields including the treatment of incurable diseases, disease modeling, tissue or organ transplantation due to the unique features of multi-potency and self-renewal. Recently, it has been found out that when stem cells are cultured in a suitable three-dimensional in vitro environment, a structure similar to the structure of an in vivo organ is formed. This structure formed to have a structure similar to an in vivo organ is referred to as an organoid.

According to organoid related technologies, theoretically, almost all types of organs can be made from only stem cells, and thus organoids are expected to be utilized for various diseases. Organoids may be more effective in testing the stability and efficacy of new drug than cell tissues made in a two-dimensional environment. Additionally, organoids may be transplanted to damaged or underdeveloped organs, and used to improve the condition of the subject. Accordingly, in terms of regenerative medicine, recently, research on organoids is on the rise, and organoids are expected to be widely used in various fields.

Since organoid maintenance and cultivation technology is in the early stage of research and has not been yet established, various researches are to be conducted on what substances are to be added during culturing or how to culture organoids effectively. The addition of R-spondin is essential in a culture medium for ex vivo culturing of organoid. However, it is difficult to isolate and purify R-spondin being a type of protein, and it is also difficult to maintain a consistent level of stability when added to the culture medium. Also, since R-spondin is an expensive substance amounting to about three million KRW per 100 µg, there is a disadvantage that the economic efficiency is poor when mass culturing organoids for use as a therapeutic agent. Therefore, there is an urgent need for an inexpensive and stable R-spondin replacement substance in order to culture clinically applicable organoids.

Technical Problem

One purpose of the present disclosure is to provide a composition for culturing an organoid. Another purpose of the present disclosure is to provide a method for culturing an organoid.

Technical Solution

One aspect of the present disclosure is to provide a composition for culturing an organoid comprising a compound of the following chemical formula 1:

[Chemical formula 1]

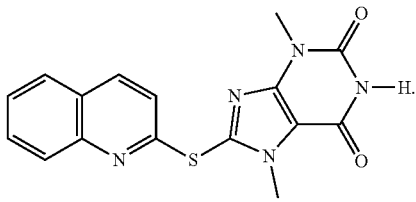

The term "organoid" refers to a cell aggregate made by aggregating and recombining cells isolated from stem cells or organ-derived cells by 3D culture, and may include organoids or cell clusters formed from suspension cell culture. The organoid may also be referred to as a small pseudo-organ, an organ analogue, or a pseudo-organ. Specifically, the organoid includes one or more cell types among various types of cells forming an organ or tissue, and should be able to reproduce the shape and function of the tissue or organ.

The term "organoid culture" includes all actions for producing or maintaining an organoid. For example, it may be differentiating stem cells or cells isolated from particular tissues into tissue or organ cells with specific functions, and/or may be surviving, growing or proliferating an organoid.

The organoid in which the composition of the present disclosure can be used may be, for example, an organoid derived from pluripotent stem cells (PSC-derived organoid), or an organoid derived from adult stem cells (adSC-derived organoid). The pluripotent stem cell may be an embryonic stem cell, a dedifferentiated stem cell, or an induced pluripotent stem cell. Preferably, the organoid may be an organoid derived from adult stem cells, and more preferably may be an organoid derived from stem cells located in the small intestinal crypt.

The organoid may be, for example, a stomach organoid, a small intestine organoid, a colon organoid, a liver organoid, a thyroid gland organoid, a lung organoid, a brain organoid, etc. Preferably, the organoid may be a small intestine organoid. In one embodiment, it is confirmed that the small intestine organoid cultured by using the composition of the present disclosure well maintains the function of small intestinal epithelial cells.

The culturing composition of the present disclosure is characterized by comprising a compound of the following chemical formula 1:

[Chemical formula 1]

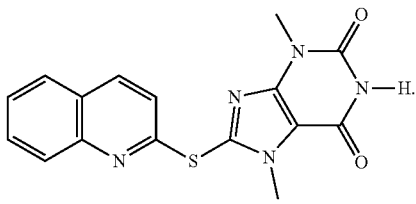

The compound of the chemical formula 1 may be substituted for an activating material of Wnt signal which has been essentially used in conventional organoid culturing. The Wnt signal is important for stem cells to play a normal role, and thus the activating material of Wnt signal is necessarily required to be added to an organoid culture. Currently, Wnt3a or R-spondin is used as the activating material of Wnt signal in order to culture organoids. In the present disclosure, the compound of chemical formula 1 can replace the Wnt3a or R-spondin when culturing organoids. In one embodiment, when organoids are cultured in a culture medium containing the compound of chemical formula 1 instead of R-spondin, their morphological characteristics, growth efficiency and marker's expression level showed similar to those of the organoids cultured in the medium containing R-spondin. Therefore, the composition may not comprise Wnt3a or R-spondin, or may comprise less than the usual concentration of Wnt3a or R-spondin which has been generally used in organoid culturing.

The concentration of the compound of chemical formula 1 comprised in the composition may be, for example, 5 to 200 μM, 6.25 to 200 μM, 6.25 to 100 μM, 10 to 100 μM, 10 to 75 μM, 20 to 75 μM, 25 to 75 μM, 20 to 50 μM, or 25 to 50 μM with respect to the total volume or amount of the composition. Preferably, the concentration of the compound of chemical formula 1 may be 20 to 75 μM, 25 to 75 μM, 20 to 50 μM, or 25 to 50 μM, and more preferably may be 25 to 75 μM, or 25 to 50 μM. Most preferably, the concentration of the compound of chemical formula 1 may be 50 μM.

The composition may be a basal culture medium for culturing organoids in which the compound of chemical formula 1 is comprised. The term "culture media" or "culture medium" means a medium which enables support for in vitro cell growth and survival, and includes all conventional culture media used in the art as being suitable for culturing cells. The culture medium and culture condition may be selected depending on the type of cultured cells. As examples for basal medium for culturing cells, Dulbecco's modified eagle's medium (DMEM), minimal essential medium (MEM), basal medium eagle (BME), RPMI1640, F-10, F-12, Glasgow's minimal essential medium (GMEM), Iscove's modified Dulbecco's medium, etc. may be used, and antibiotics such as penicillin-streptomycin or supplements, etc. may be further added as needed.

The composition of the present disclosure may further comprise an ingredient necessary for signaling pathway or organoid formation of stem cells. Specifically, the composition may further comprise one or more selected from the group consisting of epidermal growth factors (EGF), noggin, thiazovivin, CHIR99021 and a pharmaceutically acceptable salt of CHIR99021. The CHIR99021 refers to 6-[[2-[[4-(2,4-dichlorophenyl)-5-(5-methyl-1H-imidazole-2-yl)pyrimidin-2-yl]amino]ethyl]amino]-3-pyridine carbonitrile (CAS No.: 252917-06-9), which is a compound of the following chemical formula 2:

Another aspect of the present disclosure is to provide a method for culturing an organoid, comprising culturing cells in a composition containing the compound of the following chemical formula 1:

[Chemical formula 1]

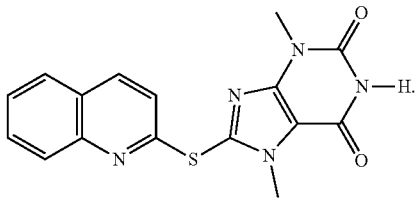

In the method for culturing organoid according to the present disclosure, the same terms as used in the composition for culturing organoid according to one aspect are used as mentioned in the above composition, unless otherwise specified.

The method for culturing organoid according to the present disclosure may comprise the steps of contacting a cell with the compound of chemical formula 1, and culturing the cell. The cell may be a stem cell, a population of stem cells, a cell differentiated from stem cells, or an isolated tissue fragment. Preferably, the cell may be an adult stem cell, and more preferably may be a cell included in or derived from small intestine crypt.

The concentration of the compound of chemical formula 1 comprised in the composition may be, for example, 5 to 200 μM, 6.25 to 200 μM, 6.25 to 100 μM, 10 to 100 μM, 10 to 75 μM, 20 to 75 μM, 25 to 75 μM, 20 to 50 μM, or 25 to 50 μM with respect to the total volume of the composition. Preferably, the concentration of the compound of chemical formula 1 may be 20 to 75 μM, 25 to 75 μM, 20 to 50 μM, or 25 to 50 μM, and more preferably may be 25 to 75 μM, or 25 to 50 μM. Most preferably, the concentration of the compound of chemical formula 1 may be 50 μM.

The composition of the present disclosure may further comprise an ingredient necessary for signaling pathway or organoid formation of stem cells. Specifically, the composition may further comprise one or more selected from the group consisting of epidermal growth factors (EGF), noggin, thiazovivin, CHIR99021 and a pharmaceutically acceptable salt of CHIR99021. The CHIR99021 refers to 6-[[2-[[4-(2,4-dichlorophenyl)-5-(5-methyl-1H-imidazole-2-yl)pyrimidin-2-yl]amino]ethyl]amino]-3-pyridine carbonitrile (CAS No.: 252917-06-9), which is a compound of the following chemical formula 2:

[Chemical formula 2]

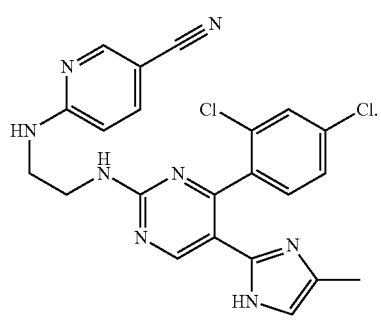

[Chemical formula 2]

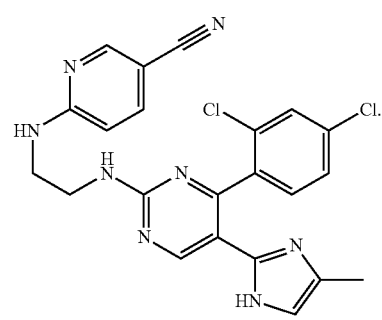

In the culturing method, the composition may not comprise Wnt3a or R-spondin, or may comprise less than the usual concentration of Wnt3a or R-spondin which has been generally used in organoid culturing.

In the composition for culturing organoid and the culturing method according to the present disclosure, it comprises a compound that can replace the protein ingredient essentially added to the conventional culture medium. Accordingly, it is possible to maintain a consistent stability when culturing organoids, and organoids can be cultured at a low cost. Therefore, the present disclosure may be utilized for mass culturing of organoids for use in the development of a therapeutic agent.

The articles "a" and "an" are used herein to refer to one or to more than one (i.e. to at least one) of the grammatical object of the article. By way of example, "an ingredient" means one ingredient or more than one ingredient.

BRIEF DESCRIPTION OF FIGURES

The patent or application file contains at least one drawing executed in color. Copies of this patent or patent application publication with color drawing will be provided by the Office upon request and payment of the necessary fee.

EXAMPLES

In the following, exemplary embodiments of the inventive concept will be explained in further detail with reference to examples. However, the following examples are meant to exemplify the present invention, and the scope of the invention is not restricted by these examples.

Example 1. Isolation of Mouse Small Intestinal Crypt

Small intestinal crypts were isolated from a mouse to be used in experiments for preparing and culturing small intestinal organoids. Specifically, the small intestine was isolated after killing a 5-7 weeks old C57BL/6 mouse weighing 20-25 g by cervical vertebrae dislocation. The small intestine was cut longitudinally from a proximal end to a distal end, and also laterally cut into pieces of about 5 mm length. The piece of small intestine obtained was washed with ice-cooled Dulbecco's phosphate-buffered saline (DPBS) until the supernatant liquid was sufficiently clear. Then, the crypts were isolated by treating with a Gentle Cell Dissociation Reagent (StemCell Technologies, Cambridge, MA), and filtering with a cell strainer.

Example 2. Screening of Compound Library Using Organoid Proliferation Measurement Compounds which can replace R-spondin in organoid cultures were screened for 8,364 types of compounds included in a representative library of the Korea Chemical Bank.

Figure 1A:
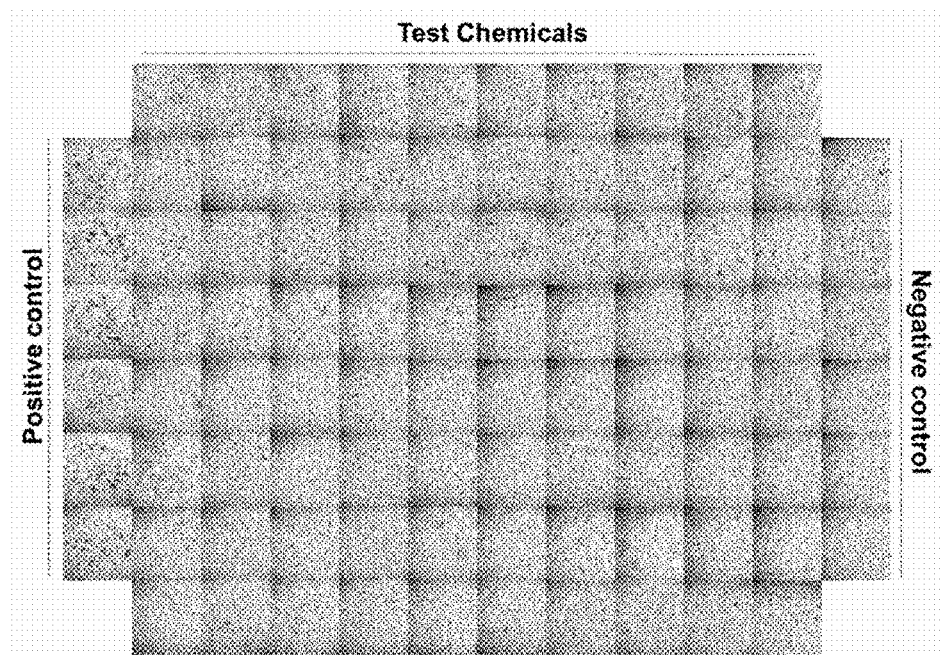
FIG. 1A is a photograph of one of 105 96-well plates used for compound screening. The six wells in the leftmost column were used as a positive control group, the six wells in the rightmost column were used as a negative control group, and the entire ten columns in the middle were used as an experimental group.

The small intestinal crypts derived from the small intestine of a 7-week-old C57BL/6 mouse isolated in Example 1 were mixed in Matrigel, and placed in each well of a 96-well plate. An experimental group of eighty wells was used per 96-well plate, three wells were used for each of the positive control group and the negative control group, and three wells were used for each of the positive control group and the negative control group including 0.5% of DMSO. The negative control group used an EN culture solution which does not contain R-spondin nor compounds (composition: advanced DMEM/F-12, Hepes buffer solution, GLUTAMAX-I SUPPLEMENT, penicillin-streptomycin solution, N-acetyl-L-cysteine, B-27 serum-free supplement, N-2 supplement, animal-free recombinant murine EGF, recombinant murine noggin, CHIR99021, thiazovivin). The positive control group used the EN culture solution in which 10% of R-spondin is contained. Hereinafter, the EN culture solution containing 10% of R-spondin is referred to as ENR culture solution. As the experimental group, 8,364 different types of compounds were added to the EN culture solution at a concentration of 50 μM, respectively. The compounds used for screening were treated immediately after completing the polymerization of matrigel and crypt, and was applied without replacement for 4 days immediately after isolating crypts. After keeping in 37° C. humidification incubator (5% $CO_2$) for 4 days, the cultured organoids were observed and optical microscope photos were taken for analysis (see FIG. 1A).

Figure 1B:
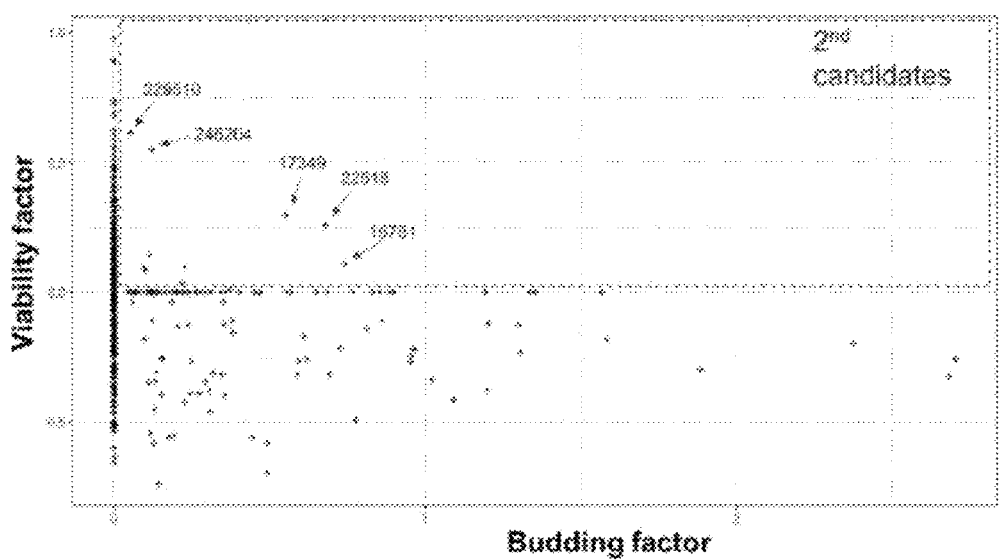
FIG. 1B shows the result of selecting a second candidate material using the total small intestinal organoid number (viability factor) and the budding small intestinal organoid number (budding factor).

The number of living organoids, the number of budding organoids, and the circumference of each organoid were measured using the optical microscope photos. For counting, a cell counter plugin of Image J Software was used, and for measuring the circumference, a free curve tool of Dixi eXcope software was used. The compounds were ranked based on the measured values, and then 295 candidate compounds were selected to be used in a second screening. The 295 candidate compounds for second screening were re-examined in the same manner as first screening. After that, 21 candidates were selected by collecting and ranking the results of the first and second screening. After performing a third screening for the 21 candidate materials in the same manner, all three results were collected to finally select seven candidate compounds (see FIG. 1B).

Figure 1C:
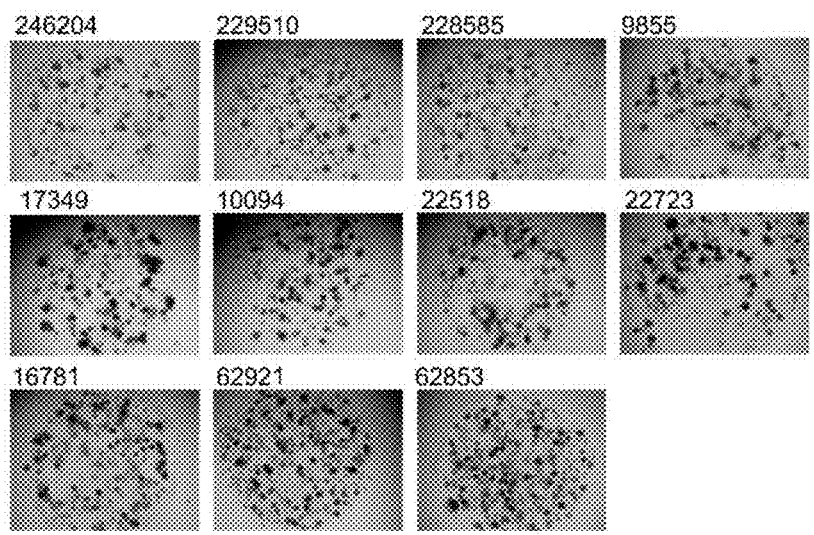
FIG. 1C is an optical micrograph of small intestinal organoid grown in a culture solution comprising a compound determined to be significant as a result of screening.

Among the final seven candidate compounds, the compound of the following chemical formula 1 (Compound Library No.: STK611777) showed the highest growth of small intestinal organoids among the candidate materials, and it was observed from numerical data and visual confirmation that said compound could grow and maintain organoids most similar to R-spondin (see FIG. 1C):

[Chemical formula 1]

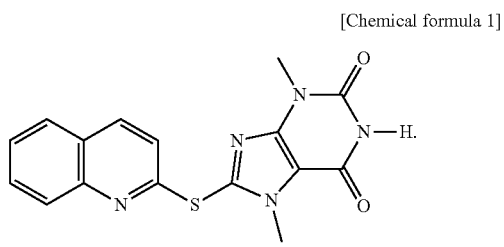

The compound is referred to as "RS-246204."

Example 3: Small Intestinal Organoid Culture Effect of RS-246204

3.1. Culture Effect According to Concentration of Compound

Figure 2A:
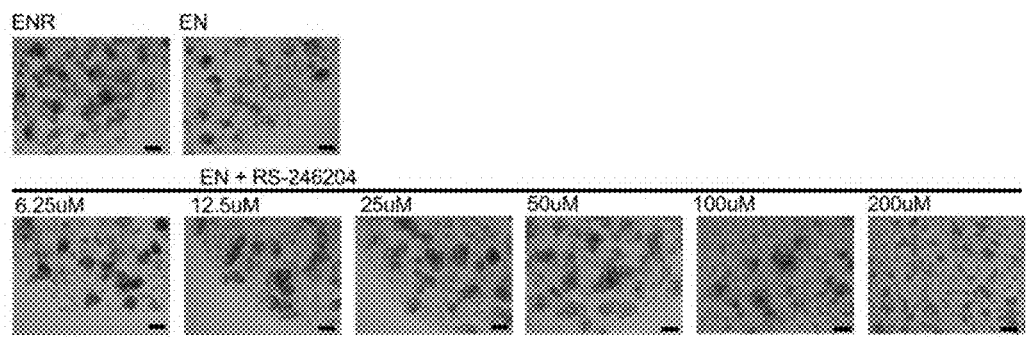
FIG. 2A is an optical micrograph of mouse intestinal crypt treated with RS-246204 and cultured for 4 days, where ENR is a positive control group (including R-spondin), EN is a negative control group, and EN+RS-246204 is an experimental group.

An optimal concentration on the small intestinal organoids culture effect of RS-246204 was examined. RS-246204 was added to the culture solution of the small intestinal crypts, respectively, at a final concentration of 6.25 μM, 12.5 μM, 25 μM, 50 μM, 100 μM, and 200 μM, and then was incubated in the culture medium for 4 days. After 4 days, it was observed that the small intestinal organoids grown in the culture solution containing 25 μM and 50 μM of RS-246024 showed similar morphology and growth to the small intestinal organoids grown of the ENR culture solution (see FIG. 2A).

3.2. WST Analysis

Figure 2B:
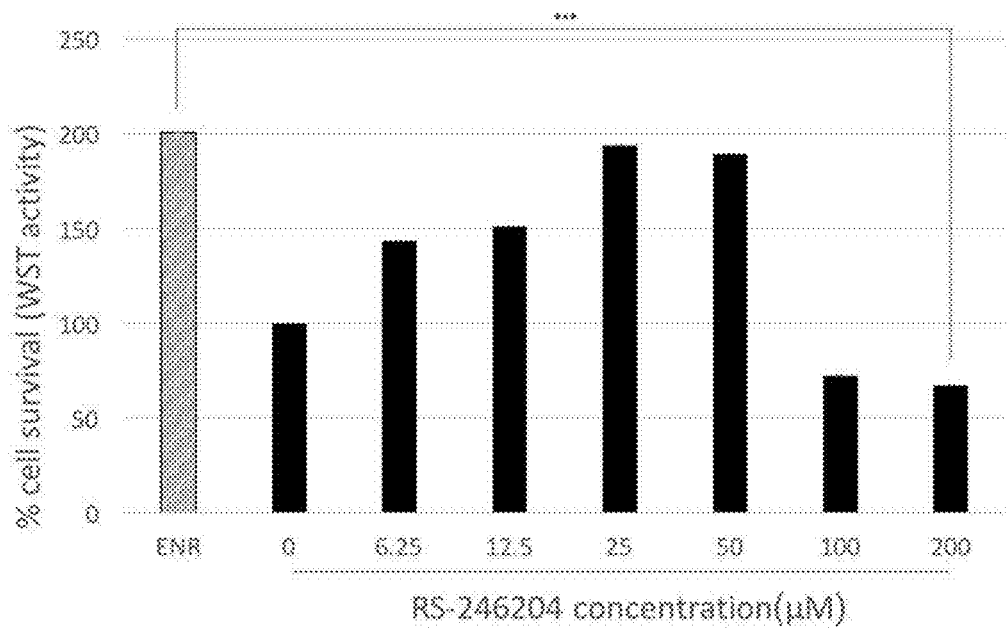
FIG. 2B is a graph showing the result of WST analysis for confirming the survival rate of small intestinal organoids according to RS-246204 concentration. The Y axis is a value obtained by converting the WST activity value into percentage, and a negative control group is set to 100%.

For more accurate confirmation, RS-246204 was treated at the same concentration, and after 4 days, 10 μl of WST was added to each well. WST is a tetrazolium salt which reacts with dehydrogenase to produce formazan, thereby causing the culture solution to become orange color. The dehydrogenase is an enzyme which exists only in a living cell, and thus it is possible to check the survival rate of cell when treated with WST. 3 hours after adding WST, only the culture solution was taken, and the absorbance was measured at 450 nm. When the survival rate in the EN culture solution, which is a negative control group, is set to 100%, the culture solution containing 25 μM and 50 μM of RS-246204 showed an organoid survival rate similar to that in the ENR culture solution, which is a positive control group (see FIG. 2B).

As a result, it was observed that when the small intestinal organoids were cultured using the isolated crypts, the small intestinal organoids grown in the culture solution in which R-spondin was replaced with RS-246204 grew in a manner similar to the small intestinal organoids grown in the conventional culture solution containing R-spondin.

3.3. Budding Characteristics and Appearance Analysis

Figure 2C:
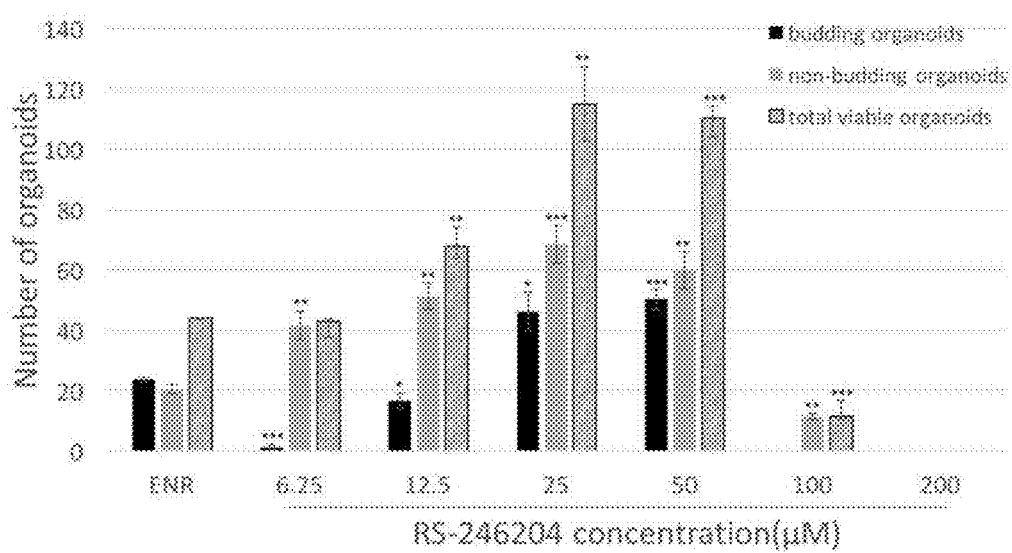
FIG. 2C is a graph showing the number of different forms of organoids after growth of small intestinal organoids according to RS-246204 concentration. The Y axis is the number of organoids present in the well. Budding organoids refer to budded organoids, and non-budding organoids refer to living organoids which have not been budded. Total viable organoids refer to a sum of the number of budding organoids and non-budding organoids.

The morphological characteristic of the small intestinal organoids is that they grow while budding. In order to check that the budding rate of the small intestinal organoids grown in the RS-246204-added culture solution (hereinafter, RS-246204 culture solution) is similar to that grown in ENR culture solution, the total number of organoids, the number of budding organoids, and the number of non-budding organoids were counted in the wells culturing for 4 days. The rate of budding organoids and non-budding organoids grown in the culture solution containing 50 μM of RS-246204 is about 1:1, which is similar to the rate of organoids grown in the ENR culture solution (see FIG. 2C). It was observed that the rate of non-budding organoids increased at a concentration lower than 50 μM, and most organoids were killed at a concentration higher than 50 μM.

Figure 2D:
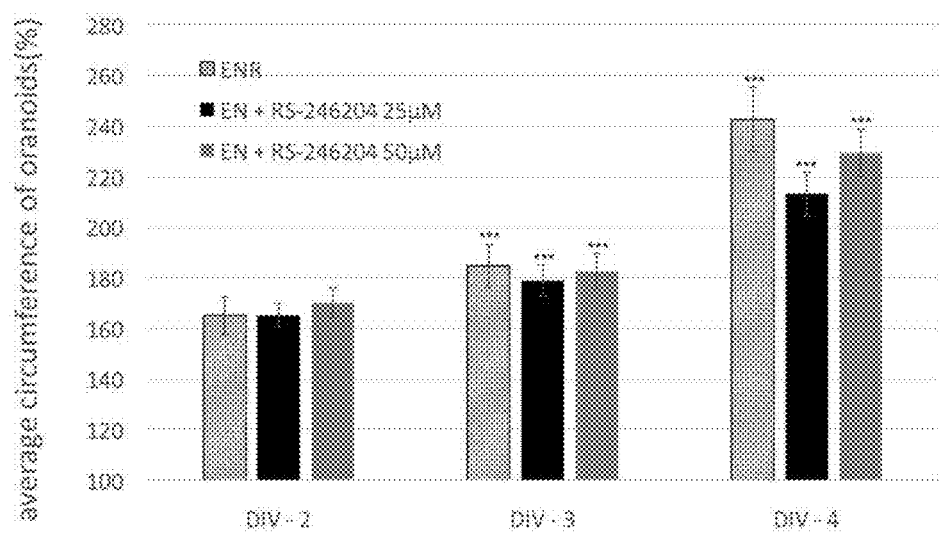
FIG. 2D is a graph measuring the average length of organoid circumference by date. In the graph, DIV refers to day in vitro, the Y axis is the percentage value of the average organoid circumference, and DIV-1 is set to 100%.

In order to check whether the growth efficiency of the small intestinal organoids grown in the RS-246204 culture solution has a difference, the small intestinal organoids cultured in each culture solution were photographed by an optical microscope every day. The circumference of the individual organoid according to the condition of culture medium and date was measured, and converted into percentage. As a result, it was observed that not only the growth efficiency but also the increase rate of the circumference according to date were also similarly observed (see FIG. 2D).

3.4. Subculture

Figure 2E:
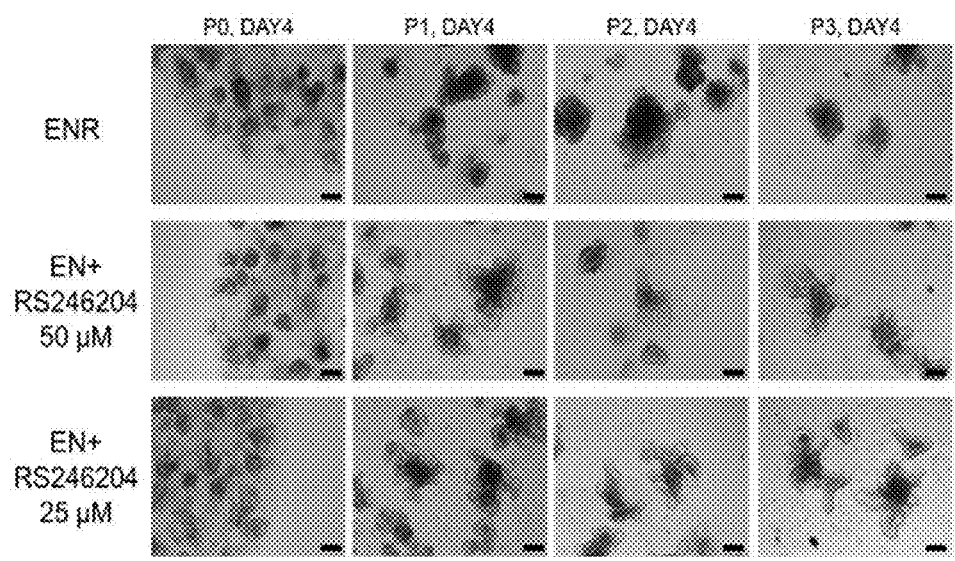
FIG. 2E is an optical micrograph of subculturing after primarily culturing small intestinal organoids under ENR and EN+RS246204 conditions, respectively.

It was confirmed that it is possible to subculture small intestinal organoids grown in RS-246204 culture solution in the same manner as small intestinal organoids grown in ENR culture solution, and it was observed that the growth and maintenance were also possible even after the subculture (see FIG. 2E). The crypts cultured in a culture solution which does not comprise R-spondin or RS-246204 could not be cultured to the small intestinal organoids.

Example 4. Analysis of Gene Expression of Small Intestinal Organoids Cultured by RS-246204

4.1. RT-PCR Analysis

Figure 3A:
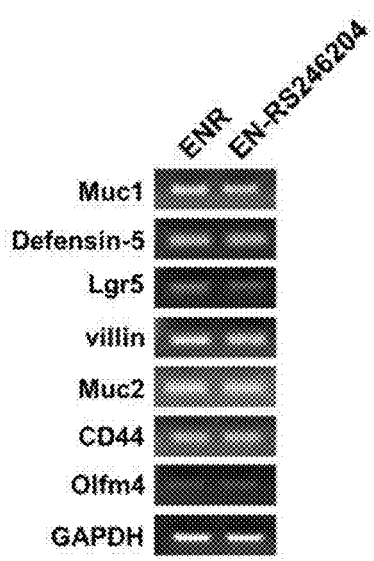
FIG. 3A is a photograph showing the result of electrophoresis after RT-PCR using RNA extracted from small intestinal organoids cultured under ENR and EN+RS246204 conditions, respectively.

In order to confirm whether lineage markers specific to the small intestinal organoids are expressed when cultured with RS-246204, RNA analysis was performed. The small intestinal organoids cultured in ENR and RS-246204 culture solutions, respectively, for 4 days were collected. RNA was extracted and cDNA was synthesized, and then RT-PCR was performed. As a marker for intestinal stem cells, goblet cells, paneth cells, enteroendocrine cells and enterocyte, RT-PCR was performed using RNA primers for Lgr5, muc-1 and muc-2, defesing-5, chromogranin A (ChgA), and villin, respectively. As a result, it was confirmed that all these cells were present in the small intestinal organoid cultured by RS-246204, and that Olfactomedin-4 (Olfm4) and CD44, which are genes located downstream of Lgr5 signaling, were also expressed (see FIG. 3A).

Figure 3B:
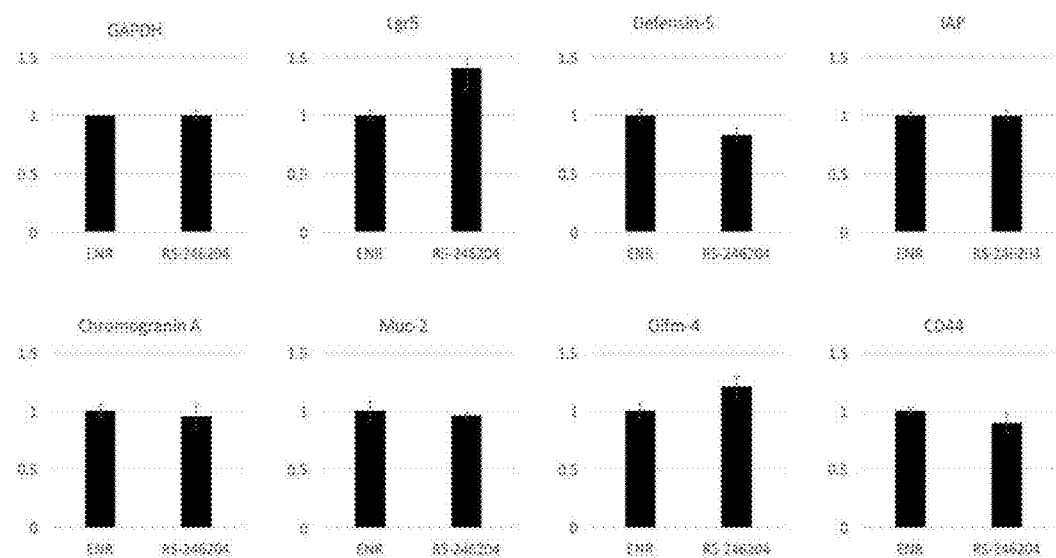
FIG. 3B is a graph showing qRT-PCR results using RNA extracted from small intestinal organoids cultured under ENR and EN+RS246204 conditions, respectively.

For quantitative analysis, qRT-PCR analysis was performed. AccuPower 2X Greenstar qPCR MasterMix (Bioneer) and Thermal Cycler Dice® Real Time System III (Takara, Japan) were used, and the reaction was performed for 10 seconds at 95° C. (denaturation), 15 seconds at 57° C. (annealing), and 20 seconds at 72° C. (extension). The RNA primers excluded Muc1 among those used in the RT-PCR test, changed the enterocyte marker from villin to Intestinal Alkaline Phosphatase (TAP), and used the same sequence for the rest. The qRT-PCR results showed that the relative amount of markers expressed showed little difference between the ENR and RS-246204 culture solutions (see FIG. 3B).

4.2. Immunofluorescence Analysis

Figure 3C:
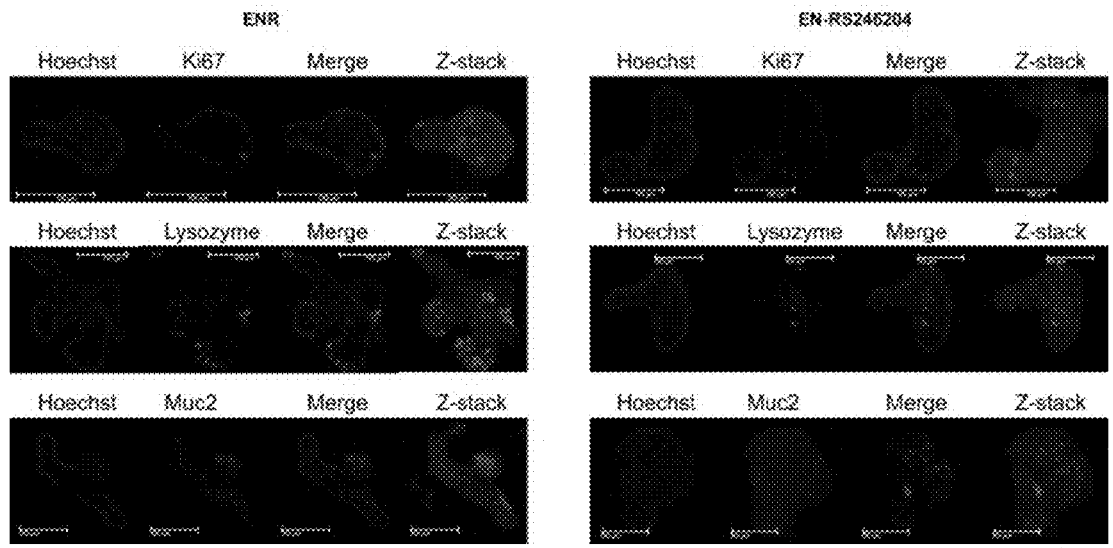
FIG. 3C shows an immunofluorescence staining results of small intestinal organoids cultured for 4 days under ENR and EN+RS246204 conditions. Hoechst (blue) represents the nucleus, and Alexa594 (red) represents the fluorescence for each antibody.

In addition, immunofluorescence staining was performed on the small intestinal organoids cultured in the ENR and RS-246204 culture solutions to confirm the expression of Muc-2, lysozyme, and Ki67, which is a marker of proliferating cells (see FIG. 3C).

Example 5. Function Maintenance of Small Intestinal Organoids Cultured by STK611777

In order to check whether functions of small intestinal epithelial cells are maintained in the small intestinal organoids cultured using the RS-246204 culture solution, CFTR agonist Forskolin analysis was performed. The forskolin is a compound which stimulates ion channels to open, thereby promoting the release of moisture. In case of small intestinal organoids, moisture gathers into the lumen by the forskolin stimulation and changes into a large spherical shape, thereby confirming the maintenance of the function of epithelial cells. After culturing for 4 days in RS-246204 culture solution and ENR culture solution, respectively, it was replaced with a culture solution to which forskolin was added at a concentration of 5 μM. Photographs were taken by an optical microscope at an interval of 10 minutes for 1 hour immediately after the replacement. Based on the optical micrographs, the free curve tool of Dixi eXcope (Korea) program was used to measure the circumference of each organoid per hour and analyze the change in circumference.

Figure 4:
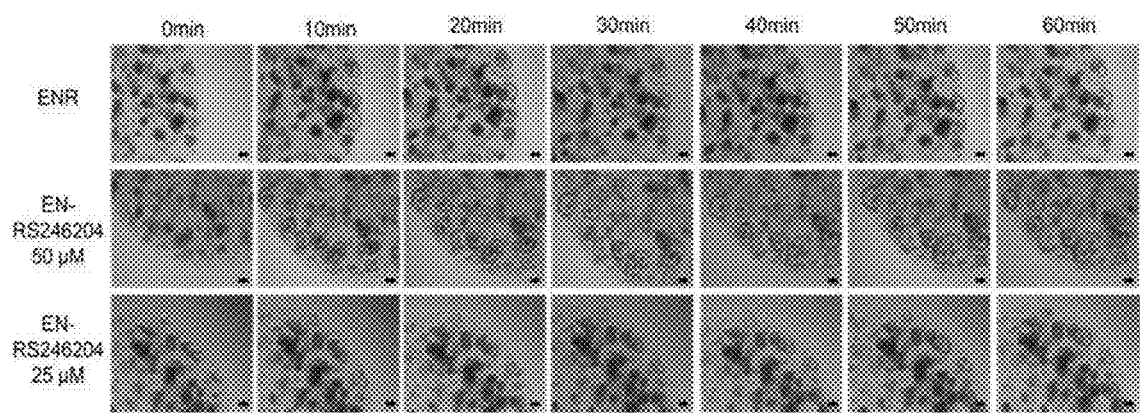
FIG. 4 is an optical micrograph of inducing forskolin stimulation after culturing small intestinal organoids for 4 days under ENR and EN+RS246204 conditions, respectively.

As a result, it was observed that the small intestinal organoids grown in RS-246204 culture solution performed well as epithelial cells, and showed a similar change in circumference to those grown in ENR culture medium (see FIG. 4).

Those skilled in the art will recognize, or be able to ascertain using no more than routine experimentation, many equivalents to the specific embodiments of the present disclosure described herein. Such equivalents are intended to be encompassed by the following claims.

What is claimed is:

1. A method for forming a human small intestinal organoid comprising: culturing (i) a human intestinal tissue fragment or (ii) cells isolated from the human intestinal tissue fragment in a composition comprising a compound of the following chemical formula 1:

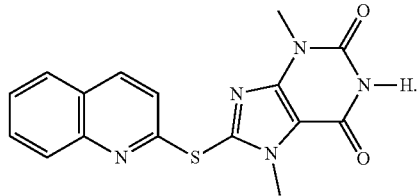

wherein a concentration of the compound in the composition is in the range of 5 μM to 100 μM.

2. The method according to claim 1, wherein the cells are stem cells.

3. The method according to claim 2, wherein the stem cells are adult stem cells.

4. The method according to claim 1, wherein a concentration of the compound in the composition is between 25 μM and 50 μM.

5. The method according to claim 1, wherein the composition further comprises one or more selected from the group consisting of epidermal growth factors (EGF), noggin, thiazovivin, CHIR99021, and a pharmaceutically acceptable salt of CHIR99021.

* * * * *